United States Patent [19]

Glover et al.

[11] 4,281,989
[45] Aug. 4, 1981

[54] ARTICULATED DENTAL HAND PIECE

[75] Inventors: Douglas L. Glover; Roger H. Rubenstein; Peter H. Douglas; Lee R. Bridges, all of Phoenix, Ariz.

[73] Assignee: The Idea Syndicate, Inc., Phoenix, Ariz.

[21] Appl. No.: 51,823

[22] Filed: Jun. 25, 1979

[51] Int. Cl.³ ............................................. A61C 1/12
[52] U.S. Cl. .................................... 433/130; 433/126; 433/115
[58] Field of Search ............... 433/130, 126, 108, 109, 433/115; 415/503

[56] References Cited

U.S. PATENT DOCUMENTS

| 623,469 | 4/1899 | Hailer | 433/130 |
| 2,453,349 | 11/1948 | Stalder | 433/130 |
| 3,727,312 | 4/1973 | Durante | 433/130 |
| 3,798,775 | 3/1974 | Weinberg et al. | 433/129 |
| 3,955,284 | 5/1976 | Balson | 433/126 |

FOREIGN PATENT DOCUMENTS

| 2334448 | 1/1975 | Fed. Rep. of Germany | 433/126 |
| 289192 | 6/1953 | Switzerland | 433/130 |

Primary Examiner—Gene Mancene
Assistant Examiner—John J. Wilson
Attorney, Agent, or Firm—Cahill, Sutton & Thomas

[57] ABSTRACT

An air driven turbine supporting a burr is pivotably mounted at the extremity of an arm, which arm is pivotably attached to the handle of a dental hand piece. Conduits extend through the handle and the arm to the turbine and provide a flow of air to and from the turbine and a flow of fluid directed into proximity of the cutting surfaces of the burr. Sealed moveable junctions at each end of the arm maintain integrity of the air and fluid flows while accommodating articulation of the hand piece.

13 Claims, 12 Drawing Figures

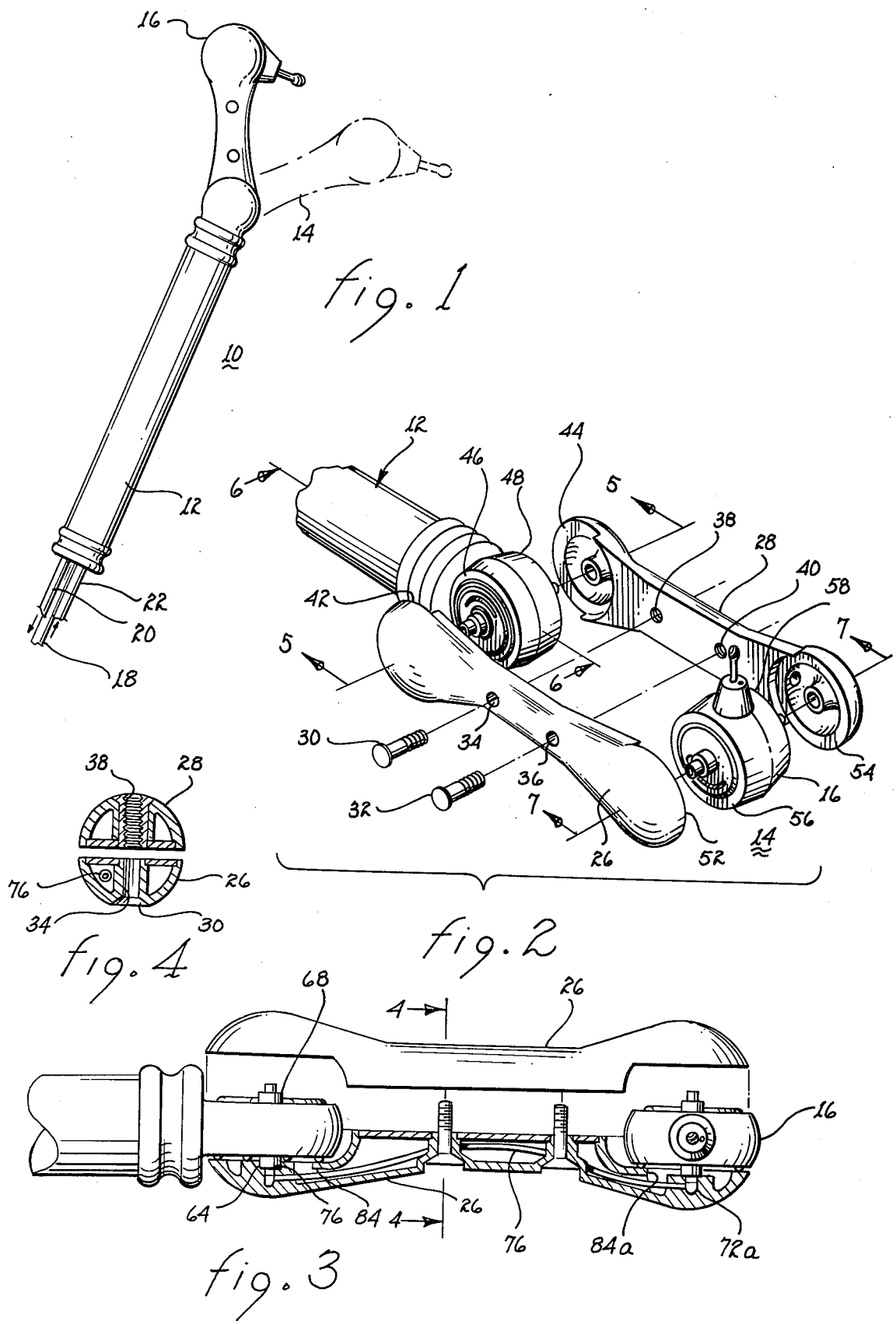

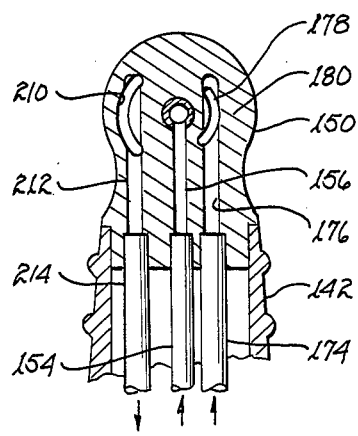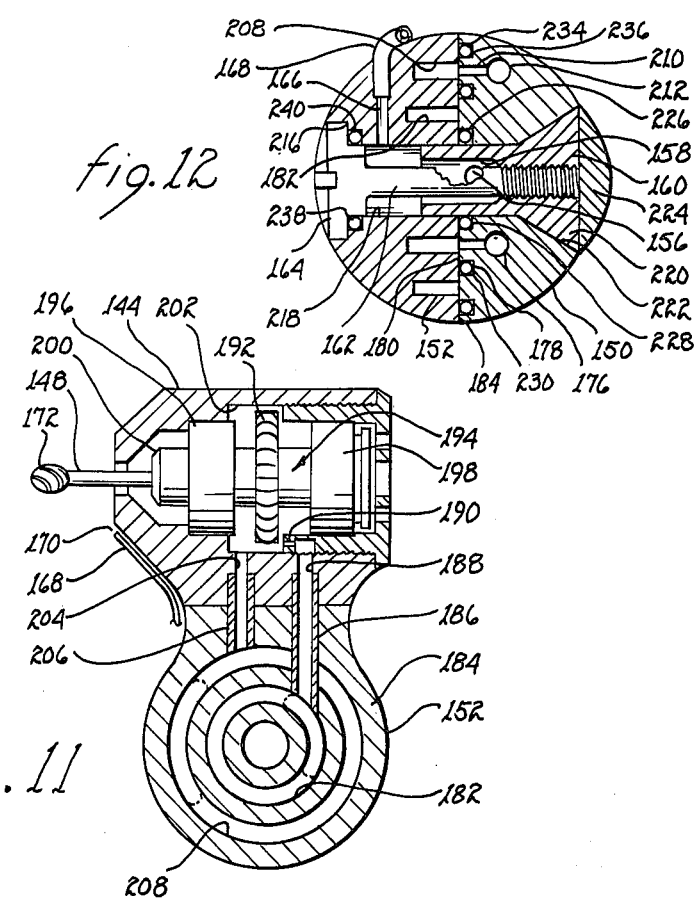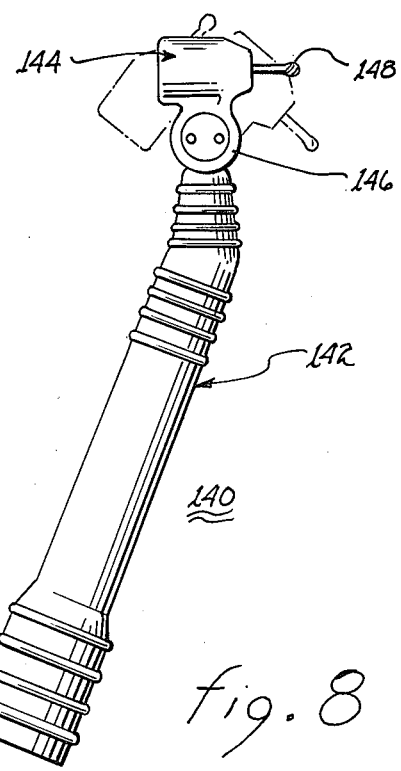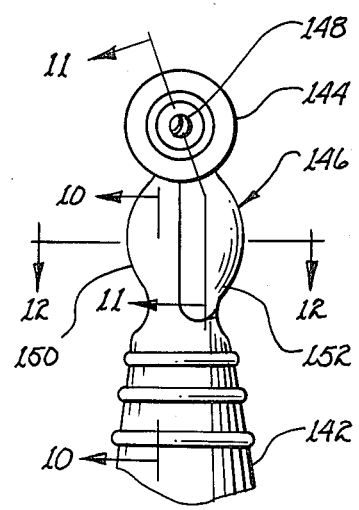

ARTICULATED DENTAL HAND PIECE

The present invention relates to dental tools and, more particulary, to air driven articulated dental hand pieces.

Conventional dental hand pieces used by dentists generally include a bend therein to set the burr at an angle other than 90° with respect to the longitudinal axis of the handle of the hand piece. Such modified alignment is of assistance to the dentist in performing the necessary drilling and polishing operations. Nevertheless, the removal by drilling, of decay, old fillings, etc., may be impossible without also requiring an attendant removal of a healthy part of the tooth. Consequently, a bigger cavity than medically necessary may result due to structural inadequacies of existing dental hand pieces.

To help resolve the structural limitations attendant conventionally configured dental hand pieces, a pivotable burr supporting head was developed in 1900 and is described in U.S. Pat. No. 662,070. The nature of the drive mechanism of this device primarily restricted movement of the head to various positions in increments of 90° with respect to a drive shaft. U.S. Pat. No. 3,509,629 describes a mechanically driven portable dental hand piece having a burr supported from a head at an obtuse angle with respect to the axis of the dental hand piece. The head itself is rotatable about the axis of the dental hand piece whereby reorientation of the head with respect to the actuating switch for the drive motor is available. U.S. Pat. No. 3,727,312 is directed to a rotatable head for a dental hand piece wherein the axis of rotation is offset from the longitudinal axis of the hand piece. Both mechanical means and pneumatic means are disclosed for rotating an attached burr.

In the last twenty or so years, substantial work has been performed to develop and refine turbine driven burrs for dental hand pieces. Usually, a flow of air is employed to impinge upon the turbine and cause rotation of the burr. Such dental hand pieces have several distinct advantages such as, very high rotational speeds of the burr, less raucous noise for the benefit of the patient, and rapid cutting by the burr with only slight application of pressure on the tooth. The following U.S. patents illustrate various embodiments of air driven dental hand pieces: U.S. Pat. Nos. 3,439,422, 3,758,948 and 3,798,775. In the dental hand pieces disclosed therein, as well as any others known to applicants, the head supporting the burr is located at a fixed angle with respect to the longitudinal axis of the dental hand piece. Thus, regardless of the angle of the hand piece, under certain circumstances it will be impossible for the dentist to remove decay, old fillings, etc., without also having to remove a healthy part of a tooth being worked on.

It is therefore a primary object of the present invention to provide an air driven articulated dental hand piece.

Another object of the present invention is to provide pivotably moveable junctions for an articulated dental hand piece which junctions preserve the flow of air and fluid therethrough.

Still another object of the present invention is to provide an articulated dental hand piece which employs a conventional turbine and burr chuck.

Yet another object of the present invention is to provide in a dental hand piece an arm readily dismantleable for cleaning purposes which arm pivotally interconnects the head and handle of the dental hand piece.

A further object of the present invention is to provide conduits for air and fluid flows within the multiple pivotally connected components of a dental hand piece.

A yet further object of the present invention is to provide a dental hand piece for setting the axis of an air turbine driven water cooled burr at an infinite angular orientation with respect to the axis of the handle while maintaining flow integrity of the air and water.

A still further object of the present invention is to provide flow integrity for air and water channeled into an incrementally laterally positionable head pivotally attached to the handle of a dental hand piece.

These and other objects of the present invention will become apparent to those skilled in the art as the description thereof proceeds.

The present invention may be described with greater specificity and clarity with respect to the following drawings in which:

FIG. 1 illustrates articulation of the dental hand piece;

FIG. 2 is an isometric view of an articulatable arm forming a part of a dental hand piece;

FIG. 3 is a partial cross-sectional view of the arm;

FIG. 4 is a cross-sectional view taken along lines 4—4, as shown in FIG. 3;

FIG. 8 illustrates a head pivotally attached to the handle of a dental hand piece;

FIG. 9 is a partial bottom view of the head and handle shown in FIG. 8;

FIG. 10 is a cross-sectional view taken along lines 10—10, as shown in FIG. 9;

FIG. 11 is a cross-sectional view taken along lines 11—11, as shown in FIG. 9; and FIG. 12 is a cross-sectional view taken along lines 12—12, as shown in FIG. 9.

Figure 5:
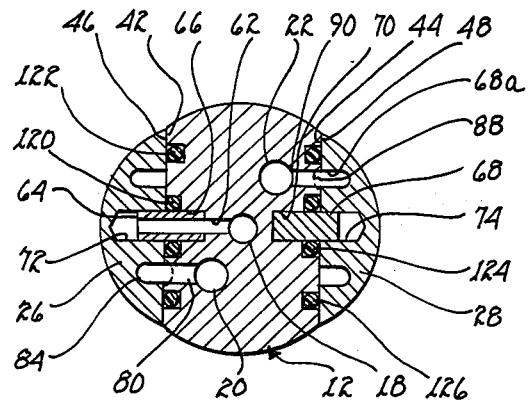
FIG. 5 is a cross-sectional view taken along lines 5—5, as shown in FIG. 2.
Figure 6:
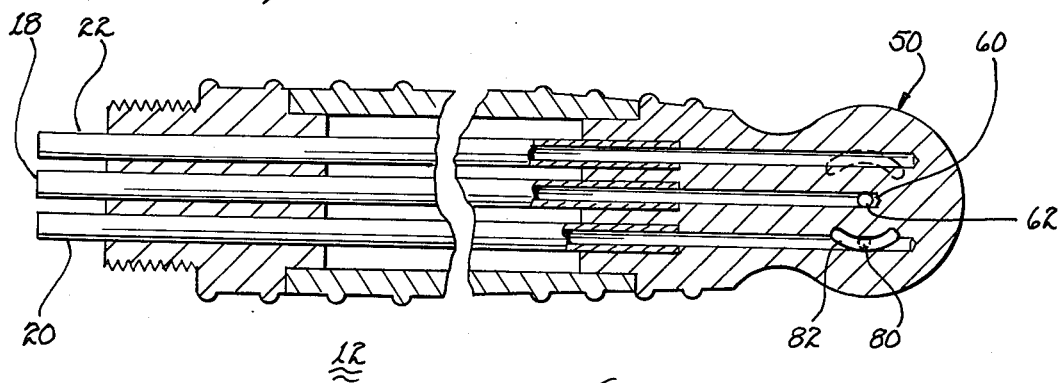
FIG. 6 is a cross-sectional view taken along lines 6—6,, as shown in FIG. 2.

Referring to FIG. 1, there is shown a dental hand piece 10 having a handle 12, a pivotally attached arm 14 and a pivotally attached head 16. A conduit 18, extending from the base of handle 12, supplies head 16 with a source of fluid under pressure. Conduit 20, also extending from the base of handle 12, provides a source of air under pressure to operate a turbine disposed within head 16 and conduit 22, extending from the base of the handle, conveys the exhaust air from the turbine to a point remote from the dental hand piece.

As illustrated in FIG. 1, arm 14 is pivotally attached to handle 12 which permits head 16 to be infinitely adjustably positionable lateral to the longitudinal axis of the handle. Head 16, being pivotally connected to the extremity of arm 14 accommodates pivotal movement thereof to permit an infinite angular orientation of an attached burr with respect to the longitudinal axis of handle. Accordingly, not only can the burr be positioned at any one of an infinite number of positions lateral to the longitudinal axis of the handle but the angular orientation of the burr with respect to the longitudinal axis of the handle may be similarly infinitely oriented. It is to be understood that other tools could be substituted for the burr; moreover, the gist of the invention can be incorporated in other than dental hand pieces.

Referring jointly to FIGS. 2, 3, 4, 5 and 6, the construction of arm 14 and connections thereto will be described. Arm 14, primarily for manufacturing economies, is split into two essentially mirror image members 26 and 28. These members are secured to one another through counter sunk bolts 30, 32 extending through holes 34, 36 and mating threaded cavities 38 and 40; other means for attachment will be readily apparent to those skilled in the art.

Arm 14 is secured to handle 12 by engagement of circular cavities 42 and 44 disposed in members 26 and 28, respectively, receiving end faces 46 and 48 of a generally cylindrical end 50 of the handle. Generally similar circular cavities 52 and 54 receive end faces 56 and 58 of generally cylindrically shaped head 16. By incorporating these circular cavities mating with commensurately shaped end faces, mechanical restrictions precluding pivotal movement in one plane of the arm with respect to the handle or pivotal movement of the head with respect to the arm are obviated.

Referring particularly to FIGS. 3, 4, 5 and 6, the channeling of the air flow into and away from head 16 and the water flow to head 16 will be described.

Water, from a source of water under pressure, is introduced to conduit 18. This conduit extends through handle 12 to a junction 60 in head 50. A passgeway 62 extends laterally from conduit 18 at a location approximately commensurate with the axis of rotation of head 50. A sleeve 64 is retained within an enlarged portion 66 of passageway 62 and protrudes beyond end face 46. This sleeve serves primarily as a bearing member for supporting pivotal movement of member 26 with respect to the handle. A stud 68 is disposed within a cavity 70 in end 50, which cavity is in axial alignment with passageway 62. The stud, protruding beyond end face 48, serves as a bearing member for member 28. Sleeve 64 and stud 68 mate with circular cavities 72 and 74 in members 26 and 28, respectively, which cavities serve in the manner of journals to pivotally receive the sleeve and stud. In addition, cavity 72 serves to receive a flow of water flowing from cavity 18 through the sleeve and into member 26. A conduit 76 interconnects with cavity 72 to channel the water through member 26 to cavity 72a, the latter being a mirror image of cavity 72. From cavity 72a, the water is conveyed into head 16 as will be described in further detail below. For reasons of economy, a conduit similar to conduit 76 may be omitted from within member 28. It is to be understood, however, that a flow through each of the members may be readily accommodated if additional volumetric flow is to occur at the burr.

Conduit 20 extends through handle 12 and introduces a flow of air to a laterally oriented passageway 80 in head 50. Passageway 80 extends laterally and terminates in a trough 82, which trough is an arcuate section having a locus upon the rotation axis of arm 14. The trough is arcuately commensurate with inlet 84 disposed in arm 26. The inlet is in fluid coommunication with the sealed interior of member 26 whereby a flow of air will extend from inlet 84 to inlet 84a adjacent head 16. Air from head 16 (see FIG. 7) is exhausted through a trough 86 in member 28, which trough is arcuate and radially commensurate with inlet 84 in member 26. As member 26 is a sealed hollow, any air flowing into inlet 86 will flow out of an inlet disposed in the other end of the member and positionally commensurate with an arcuate trough 88 disposed in face 48 of handle 12. Trough 88 interconnects with conduit 22 through lateral passageway 90. Thereby, air is introduced from the handle through member 26 to head 16 to provide power to spin the turbine within the head and the air is exhausted from the head through member 28 into conduit 22 within handle 12.

It may be noted that as members 26 and 28 are essentially duplicates of one another except for the attachment means (holes 34 and 36 and threaded cavities 38 and 40), the non-used inlets, passageways may be sealed off by planar surfaces at end 50 and head 16, indicated in the various figures.

Figure 7:
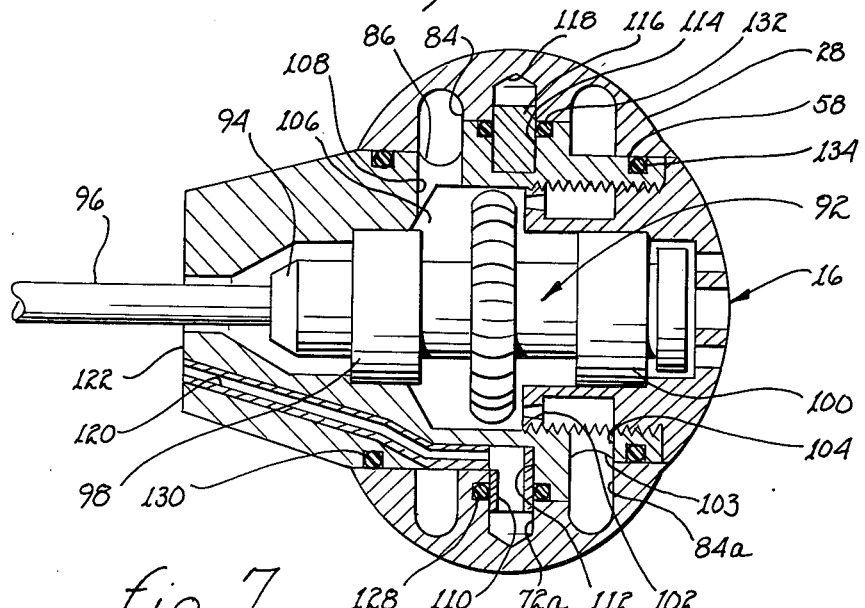
FIG. 7 is a cross-sectional view taken along lines 7—7, as shown in FIG. 2.

Referring particularly to FIG. 7, head 16 will be described. A conventional and commercially available turbine 92 having a chuck 94 for receiving a burr 96 is rotatably mounted within head 16 by means, such as bearings 98 and 100. A nozzle 102 is in fluid communication with trough 103 disposed in end face 56 of the head through a passageway 104. The trough is in fluid communication with inlet 84a whereby the air flowing therefrom is channeled to and through the nozzle. The air flowing out of nozzle 102 strikes impeller 105 to drive turbine 92 and thereafter is exhausted into chamber 106. Chamber 106 is in fluid communication with trough 86 in member 28 through a short passageway 108. From the trough, the exhausted air is conveyed through member 28 into conduit 22 and ultimately discharged.

The fluid flowing into cavity 72a from conduit 76 is introduced into sleeve 110 mounted within and extending from cavity 112 in head 16. A similar axially commensurate cavity 114 is disposed in the other side of head 16 to receive stud 116, which stud is rotatably mounted within cavity 118 in member 28. Both the sleeve and the stud serve the function of journal members to permit rotation thereabout of head 16 with respect to arm 14. A conduit 120 is disposed within head 16 and extends from cavity 76a to channel water flowing through sleeve 110 to end 122 of the head. The orientation of conduit 120 is such that the water ejected therefrom under pressure will impinge upon or in proximity to the cutting surfaces of burr 96.

Various O-rings or other seal means, such as O-rings 120 and 122 in end face 46, O-ring 124 and 126 in end face 48, O-ring 128 and 130 in end face 52 and O-rings 132 and 134 in end face 54 may be employed to effect radial seals about each of the air and fluid flow junctions.

Although not specifically illustrated in the drawings, switch means for controlling or otherwise regulating the flow of air and fluid through the head may be incorporated within handle 12. In the alternative, such switch means may be foot operated or disposed upon an attendant console.

From the above description of the present invention, it will become apparent that all of the benefits attendant air driven turbine powered burrs are incorporated. Moreover, orientation of the axis of the burr is infinitely adjustable with respect to the longitudinal axis of the handle within a relatively large angular and laterally positionable range. This latitude aids a dentist in minimizing the amount of healthy tooth that will be drilled regardless of the location or angular orientation of any drilling that may need to be done upon a tooth.

A variant 140 of the present invention is illustrated in FIG. 8. Herein, the handle of a dental hand piece 142 supports a head 144 through a pivoting junction 146. An air driven burr 148, or the like, is supported by and extends from the head. As noted in phantom lines, the head is reorientable with respect to the hand piece and thereby provides angular reorientation for the burr to accommodate almost any drill angle sought.

As illustrated in FIG. 9, junction 146 is formed of two mating members 150 and 152 pivotally secured to one another; member 150 is rigidly attached to the dental hand piece while member 152 rigidly extends from head 144.

The structural details attendant the transport of air to and from the head through the hand piece and transport of water to the head will be described with joint reference to FIGS. 10, 11 and 12. Water under pressure is transported through conduit 154 in hand piece 142 to passageway 156 in member 150. The passageway terminates in fluid communication with an annular cavity 158 formed by threaded insert 160 through which shank 162 of bolt 164 extends. A further passageway 166 in member 152 channels the water into a conduit 168 having an outlet 170 directing a stream of water toward tip 172 of burr 148.

A flow of air is introduced through conduit 174 in hand piece 142, which conduit is in fluid communication with passageway 176 in member 150. Passageway 176 is in fluid communication with an arcuate trough 178 disposed in end face 180 of member 150. A cylindrical plenum 182 is disposed in end face 184 of member 152, which plenum, on attachment of members 150 and 152, is in fluid communication with arcuate trough 178. A conduit 186 extends from plenum 182 to direct air into passageway 188 in head 144. Passageway 188 is in fluid communication with nozzle 190, which nozzle directs a stream of air against turbine 192 of turbine assembly 194. The turbine assembly may be a conventional turbine assembly supported by bearings 196 and 198 in head 144. The turbine assembly, through a chuck 200, supports burr 148.

After the air has passed through turbine 192, it enters cavity 202. Passageway 204 and interconnecting conduit 206 channel the air from the cavity to cylindrical plenum 208 disposed in end face 184 of member 152. The cylindrical plenum, upon mating of members 150 and 152, is in registration with arcuate trough 210 disposed in end face 180 of member 150. A passageway 212 conveys air exhausted into the arcuate trough to conduit 214 disposed in hand piece 142.

It is to be understood that conduit 174 is in communication with a source of air under pressure and that conduit 154 is in communication with a source of water under pressure. Conduit 214 conveys the exhaust air to a suitably located exhaust port to vent the exhaust air.

Members 150 and 152 are retained adjacent one another by means of a bolt 164 having a head resting against a recessed shoulder 216. The bolt extends through a central cavity 218 in member 152, which cavity also receives the centrally recessed portion of threaded insert 160. The threaded insert includes a splayed end 220 mating with a counter sunk shoulder 222 formed as part of a centrally located passageway extending through member 150. As illustrated in FIG. 12, threaded insert 160 threadedly engages bolt 162 to draw members 150 and 152 toward one another and maintain the end faces thereof adjacent one another. A cap 224 may be employed to seal the threaded cavity in the threaded insert.

To maintain integrity of the air and water flows through junction 146, O-rings may be employed. In example, an O-ring 226 may be disposed within an annular channel 228 disposed in member 150 and bearing against end face 184 of member 152 and against the exterior surface threaded insert 160. An O-ring 230 may be disposed in annular channel 232 disposed in end face 180 of member 150 and intermediate cylindrical plenums 182 and 208. A further O-ring 234 may be disposed in annular channel 236 disposed in end face 180 of member 150 and radially external to cylindrical planum 208. To seal cavity 218, O-ring 238 may be disposed in annular cavity 240 in shoulder 216 and bearing against the under surface of the head of bolt 164.

From the above description of variant 140, several factors will be readily apparent. First, the head is attached to the dental hand piece in such a manner as to permit infinite incremental angular reorientation of the head with respect to the dental hand piece. Second, reorientation of the head will not affect or destroy the integrity of the intake and exhaust air necessary to operate the turbine mounted within the head. Third, water is conveyed to a point in proximity to the supported burr at any angular orientation of the head without incurring water leakage at the junction between the head and the dental hand piece. Fourth, the variant permits a dentist to use a turbine driven burr to drill formerly inaccessible areas. And, fifth, the variant permits a dentist to orient the burr with respect to the dental hand piece so as to minimize drilling and removal of sound tooth.

While the principles of the invention have now been made clear in an illustrative embodiment, there will be immediately obvious to those skilled in the art many modifications of structure, arrangement, proportions, elements, materials, and components, used in the practice of the invention which are particularly adapted for specific environments and operating requirements without departing from those principles.

We claim:

1. An articulated dental hand piece, said articulated dental hand piece comprising in combination:
   (a) a handle having a longitudinal axis for manually grasping and manipulating said dental hand piece;
   (b) a head for rotatably supporting an air turbine driven burr;
   (c) arm means comprising a pair of mating members for articulatably interconnecting said handle and said head;
   (d) pivot means disposed at the interconnctions between said handle, said head and said arm means for pivotally repositioning each of said handle and said head with respect to said arm means;
   (e) conduit means for channeling an air flow from said handle, via said arm means and into said head for powering the burr supporting turbine, one member of said pair of members comprising a segment of said conduit means;
   (f) further conduit means for channeling the air exhausted from the turbine, another member of said pair of members comprising a segment of said further conduit means;
   (g) water conduit means for channeling a flow of water from said handle, through said arm means and into said head for discharge in proximity to the burr;

whereby, said head is laterally and angularly positionable with respect to the longitudinal axis of said handle.

2. The dental hand piece as set forth in claim 1 including seal means disposed at each of said pivot means for maintaining integrity of the air flow to the turbine.

3. The dental hand piece as set forth in claim 1 wherein a segment of said water conduit means is disposed within one of said members.

4. The dental hand piece as set forth in claim 1 wherein said segment of each of said members comprises a hollow section.

5. The dental hand piece as set forth in claim 4 including first journal means disposed intermediate said handle and said arm means and second journal means disposed intermediate said head and said arm means.

6. The dental hand piece as set forth in claim 5 wherein said water conduit means includes said first and second journal means.

7. The dental hand piece as set forth in claim 6 wherein said conduit means includes:
   (i) a first aperture and a mating first trough disposed at the junction of said handle and said arm means; and
   (ii) a second aperture and a mating second trough disposed at the junction of said arm means and said head;

and, wherein said further conduit means includes:
   (i) a third aperture and a mating third trough disposed at the junction of said head and said arm means; and
   (ii) a fourth aperture and a mating fourth trough disposed at the junction of said arm means and said handle.

8. The dental hand piece as set forth in claim 7 including seal means for preventing leakage of the air and water flows at the junctions between said handle and said arm means and between said arm means and said head.

9. A dental hand piece for supporting an air turbine driven burr, said dental hand piece comprising in combination:
   (a) a handle;
   (b) a head for supporting the burr;
   (c) a junction for pivotally interconnecting said handle and said head, said junction comprising;
      (i) a first member extending from said handle, said first member including an end face;
      (ii) a second member extending from said head, said second member including an end face; and
      (iii) means for urging said end faces of said first and second members adjacent one another during pivotal movement of said head with respect to said handle;
   (d) first means for channeling a flow of air from said handle, through said junction and into said head, said first channeling means comprising a first cylindrical cavity disposed in one of said end faces and a mating arcuate trough radially coincident with said first cylindrical cavity disposed in another of said end faces;
   (e) second means for channeling a flow of exhaust air from said handle, through said junction and into said handle, said second channeling means comprises a second cylindrical cavity disposed in one of said end faces and a mating arcuate trough radially coincident with said second cylindrical cavity disposed in another of said end faces;
   (f) third means for channeling a flow of fluid from said handle, through said junction into said head and to a point proximate the tip of the burr; and
   (g) means for maintaining the integrity of said first, second and third channeling means in said junction.

10. The dental hand piece as set forth in claim 9 wherein said maintaining means includes a threaded bolt extending from one side of said junction and a mating threaded insert disposed in the other side of said junction.

11. The dental hand piece as set forth in claim 10 wherein said third channeling means includes an annular cavity disposed about said bolt.

12. The dental hand piece as set forth in claim 11 wherein said maintaining means includes a plurality of O-rings disposed intermediate the end faces of said first and second members for precluding flow intermediate said first, second and third channeling means.

13. The dental hand piece as set forth in claim 12 wherein said maintaining means further includes seal means for precluding flow out of said junction adjacent said bolt.

* * * * *